(12) United States Patent
Boll

(10) Patent No.: US 8,445,029 B2
(45) Date of Patent: May 21, 2013

(54) PLASMA-ADAPTED FULL ELECTROLYTE SOLUTION

(75) Inventor: Michael Boll, Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 85 days.

(21) Appl. No.: 13/201,321

(22) PCT Filed: Mar. 8, 2010

(86) PCT No.: PCT/EP2010/052895
§ 371 (c)(1),
(2), (4) Date: Aug. 12, 2011

(87) PCT Pub. No.: WO2010/102972
PCT Pub. Date: Sep. 16, 2010

(65) Prior Publication Data
US 2011/0311644 A1    Dec. 22, 2011

(30) Foreign Application Priority Data
Mar. 13, 2009   (DE) .......................... 10 2009 012 671

(51) Int. Cl.
*A01N 59/26*   (2006.01)
*A61K 33/42*   (2006.01)

(52) U.S. Cl.
USPC ...................................................... 424/602

(58) Field of Classification Search
None
See application file for complete search history.

(56) References Cited

U.S. PATENT DOCUMENTS

| | | | |
|---|---|---|---|
| 3,821,368 A * | 6/1974 | Reynolds | 424/605 |
| 4,308,255 A | 12/1981 | Raj et al. | |
| 5,955,257 A | 9/1999 | Burger et al. | |

FOREIGN PATENT DOCUMENTS

| | | |
|---|---|---|
| DE | 3224823 A1 | 1/1984 |
| EP | 0613688 A1 | 9/1994 |
| JP | 6172191 A | 6/1994 |
| WO | WO0194349 A1 | 12/2001 |

OTHER PUBLICATIONS

Morgan, Crit. Care and Resuscitation 5: 284 (2003).*
DiBartolo, Metabolic acid-base disorders in Fluid Therapy in Small Animal Practice, 2000, p. 211.*
Article with English Abstract—Andreu et al., "Introduction of platelet additive solutions in transfusion practice," *Transfus. Clin. Biol.*, vol.14(1), May 2007, pp. 100-106.
Article—Allen I. Arieff, "Postoperative hyponatraemic encephalopathy following elective surgery in children," *Paediatric Anaesthesia*, vol. 8, 1998, pp. 1-4.
Article—Joachim Boldt, "Saline versus balanced hydroxyethyl starch: does it matter," *Transfusion Alternatives in Transfusion Medicine*, vol.9, No. 3, Sep. 2007, pp. 189-197.
Article—Druml, "Warum sind die Infusionslösungen so (schlecht) zusammengesetzt? Eine historische Perspektive," *Wiener Klinische Wochenschrift, The Middle European Journal of Medicine*, vol. 117, No. 3, 2005, pp. 67-70.
Article with English Abstract—Zander et al., "Requirements and expectations for optimal volume replacement," *Anasthesiol Intensivmed Notfallmed Schmerzther*, vol. 40, No. 12, Dec. 2005, pp. 701-719.
Search Report for PCT/EP2010/052895 dated Jun. 15, 2010, 3 pages.

* cited by examiner

*Primary Examiner* — James H. Alstrum-Acevedo
*Assistant Examiner* — Thor Nielsen
(74) *Attorney, Agent, or Firm* — Dority & Manning, P.A.

(57) ABSTRACT

The present invention describes a balanced aqueous electrolyte solution. In particular, a balanced aqueous electrolyte solution that is particularly suitable as a solution for intravenous and subcutaneous infusion because of its being plasma-adapted is described. In addition to the balanced electrolyte solution itself, an electrolyte mixture as well as a process for preparing the balanced electrolyte solution from this mixture, and a medicament comprising the solution and optionally an active ingredient are provided.

18 Claims, No Drawings

PLASMA-ADAPTED FULL ELECTROLYTE SOLUTION

CROSS REFERENCE TO RELATED APPLICATION

This application is the national stage entry of International Patent Application No. PCT/EP2010/052895 having a filing date of Mar. 8, 2010, which claims priority to and the benefit of German Patent Application No. 102009012671.6 filed in the German Intellectual Property Office on Mar. 13, 2009, the entire contents of which are incorporated herein by reference.

The present invention relates to a balanced aqueous electrolyte solution. In particular, the present invention relates to a balanced aqueous electrolyte solution that is particularly suitable as a solution for intravenous and subcutaneous infusion because of its being plasma-adapted. In addition to the balanced electrolyte solution itself, an electrolyte mixture as well as a process for preparing the balanced electrolyte solution from this mixture, and a medicament comprising the solution and optionally an active ingredient are provided.

The intravenous administration of salt solutions to patients ("drip") is the most common infusion treatment performed in the preclinical field of emergencies and accidents, in the clinical field (everywhere), in the practices of office-based physicians, and increasingly in senior citizens care facilities. It is applied when the patients exhibit an acute lack of fluid in the extracellular space that the patients are not able, willing or supposed to remedy fast enough by drinking, such as due to a disturbance of the sensation of thirst, or due to a required peristalsis inhibition in the gastrointestinal tract. Such salt solutions are infused, in particular, in order to compensate acute losses of fluid caused, for example, by vomiting or diarrheas, or shock-induced dehydrations in the circulation, or blood losses. The latter is done in part only temporarily until colloidal volume replacement solutions or blood preparations are available. The salt solutions to be used in all those cases are preferably balanced electrolyte solutions, i.e., solutions that should ideally contain all the electrolytes occurring in the human blood plasma, i.e., in the quantitative proportions and osmotically active concentrations prevailing therein.

Further, such salt solutions are extensively used for dissolving or diluting drugs, nutrients or additional minerals that are to be administered intravenously, and infusing them at a defined constant rate ("carrier solutions").

Such infusion therapies as we understand it today were realized only in the 20th century, and have become widely customary since World War II. However, it was common for a long time in Europe that the infusion solutions were mixed by the hospitals themselves before use and heated for sterilization. Later, the solutions were standardized and formulated by the respective hospital pharmacies. In the last three decades, this has been done by the industry, mainly for cost reasons (W. Druml, Wien. Klin Wochenschr. 2005, 117/3, 67-70).

The challenge in the preparation and formulation of such balanced electrolyte solutions for the substitution of extracellular fluid and electrolytes resides in the fact that, on the one hand, the physiological electrolyte pattern of the plasma is to be essentially mimicked, i.e., the concentrations of the cations (sodium, potassium, calcium and magnesium) and of the anions (chloride, phosphate and hydrogencarbonate) in accordance with their importance [Zander et al., Anästhesiol. Intensivmed. Notfallmed. Schmerzther. 2005, 40, 701-719], but on the other hand, restrictions resulting for technological and clinical reasons are to be observed. Already for galenic and other reasons, especially because of the instability of hydrogencarbonate during heat sterilization and during use in common plastic containers, the demand for a plasma-identical hydrogencarbonate content can be fulfilled only partially. In the end, this can be achieved by employing hydrogencarbonate precursors instead of hydrogencarbonate or its theoretically suitable salts as such. Organic anions, such as lactate, acetate or others, that are metabolized into hydrogencarbonate only upon infusion in the organism and thus provide it there are suitable for this purpose. Apart from the problems associated with the lack or replacement of hydrogencarbonate, the osmolality of the respective solutions should match that of the blood plasma in order that undesirable fluid relocations between the intra- and extracellular spaces are avoided. In addition, the solutions intended for intravenous infusion must not possess any significant acidity or alkalinity for the purpose of ensuring a good local tolerability upon infusion, and moreover, they must be composed in a way that does not alter the physiological acid-base balance. Finally, there is the problem that the blood plasma contains certain proteins that are not themselves part of balanced electrolyte solutions, but whose negative charges require the presence of counter ions for reasons of electroneutrality, which cannot be mimicked identically in the protein-free electrolyte solutions.

Therefore, all the balanced electrolyte solutions currently in use are a compromise between the demand for an ideal plasma-identical electrolyte pattern and that really present in the solution, and do not meet the other requirements mentioned, or only incompletely so. The discrepancy between the ideal and real compositions is enhanced by the fact that any increased effort to comply with individual elements must necessarily lead to the neglect of other elements.

Due to the historical development mentioned above, in the course of which infusion solutions were prepared in the hospital area itself on a local basis, there now exist a wide variety of infusion solutions of different compositions attempting to deal with the problems mentioned, each in its own way. However, a 0.9% sodium chloride solution (saline) has become established initially as the most frequently applied infusion solution in infusion therapy already for reasons of production technology, such as simple preparation and low cost. Further, there are solutions containing other electrolytes in addition to sodium chloride, such as Ringer and Hartmann solutions, named after their creators, and lactated Ringer (LR) solution, which like the Hartmann solution contains lactate ions. Table 1 compares the compositions of these infusion solutions with the electrolyte content of human blood plasma (J. Boldt, Transfusion Alternatives in Transfusion Medicine, 2007, 9, 189-197).

TABLE 1

Compositions of different infusion solutions. The individual compositions vary depending on the manufacturer and country of origin.

| Electrolytes | Plasma | 0.9% NaCl | Ringer | LR | PlasmaLyte 148 | Hartmann |
|---|---|---|---|---|---|---|
| $Na^+$ [mmol/l] | 140 | 154 | 154 | 131 | 140 | 129 |
| $K^+$ [mmol/l] | 4.2 | — | 4.0 | 5.4 | 5 | 5 |
| $Ca^{2+}$ [mmol/l] | 2.5 | — | 2.3 | 1.8 | — | 4 |
| $Mg^{2+}$ [mmol/l] | 3 | — | — | 0.5 | 3 | — |
| Phosphate [mmol/l] | 1.25 | — | — | — | — | — |
| $Cl^-$ [mmol/l] | 103 | 154 | 163 | 112 | 98 | 109 |
| Lactate [mmol/l] | 1 | — | — | 27 | — | 29 |
| Acetate [mmol/l] | — | — | — | — | 27 | — |
| $Na^+/Cl^-$ ratio | 1.36 | 1.0 | 0.94 | 1.17 | 1.42 | 1.18 |

As can be seen from Table 1 upon comparison with the composition of plasma, the stated solutions are in part not "physiological" because they consist of a non-physiological mixture of electrolytes, i.e., one that does not correspond to the quantitative ratios in the blood plasma, or exhibit another osmolality than that of blood plasma, or other differences.

In addition, in part significant side effects of these solutions are known, or complications during the use of the infusion solutions were reported. Thus, considerable changes in the acid-base balance of patients are observed who are infused large amounts of such salt solutions containing no hydrogencarbonate, or in which the chloride to sodium ratio is above that of the blood plasma. Depending on the point of view, this phenomenon is classified as "dilution acidosis" or "hyperchloremic acidosis". As mentioned before, although the lack of hydrogencarbonate can be compensated by using certain organic anions that are metabolized into hydrogencarbonate and substitute it in a secondary way, the amounts of organic anions required for this purpose are smaller than would be desirable to be able to lower the proportion of inorganic anions, such as chloride, to a plasma-identical level. Therefore, when chloride anions are partially replaced by hydrogencarbonate-providing organic anions, either a hyperchloremic acidosis cannot be fully prevented, or when higher concentrations of hydrogencarbonate-providing anions are used, there is a risk that an alkalosis occurs as a result of the infusion on unsuitably composed infusion solutions.

Other complications are in part due to the fact that the osmolality of many currently used electrolyte solutions is below that of the blood plasma and thus so-called "free water" is supplied in excess. "Free water" means fluid that is not bound by a corresponding ion fraction. Upon intravenous infusion, "free water" penetrates increasingly into body tissues and favors the formation of fluid accumulations ("edemas") therein. Brain cells are especially sensitive to changes in osmolality, which is manifested by cerebral symptoms ranging from somnolence to encephalopathy or even coma. Especially in premature and full-term babies, in whom the brain mass makes up a disproportionately high share of the body weight as compared to adults, a brain edema can occur particularly easily. When larger quantities of "free water" are supplied in the form of hypotonic infusion solutions, or infusion solutions having too low an osmolality as compared to the blood plasma, even deaths have been described especially in pediatrics (A. I. Arieff, Paediatric Anaesthesia, 1998, 8, 1-4). Patients with a head injury are also particularly endangered, because there is a risk that a brain edema is aggravated or that the brain pressure increases when they are treated with hypotonic infusion solutions. A typical representative of a hypotonic infusion solution is the widely used lactated Ringer solution, for example. Another disadvantage of this type of solution associated with possible complications is the fact that the lactate contained in the solution cannot be metabolized into hydrogencarbonate if there is severe liver damage, which is frequently the case in severely ill intensive care patients or patients in heavy shock.

Further, undesirable side effects of the infusion of commercially available infusion solutions, such as poor local tolerabilities and problems of compatibility with admixed medicaments, have been known. Thus, the university and commercial research aims at the development and preparation of electrolyte solutions suitable for infusion that correspond to the physiological electrolyte profile of plasma, can be heat-sterilized in the preparation process, exhibit a high local tolerability and high compatibility with added medicaments, have the same osmolality as plasma, and do not affect the acid-base balance.

Thus, DE 32 24 823 A1 describes a process for preparing an electrolyte solution optimized for the respective individual disease for application in hemodialysis. The preparation is started with 9 liters of a parent solution containing 45.5 val of sodium ($Na^+$), 350 mval of magnesium ($Mg^{++}$), 12.25 val of acetate ($CH_3CO_2^-$) and 33.6 val of chloride ($Cl^-$) and optionally from 630 to 720 g of glucose. The intended final content is adjusted by filling up the volume necessary to reach 10 liters with sterile units of 3.5 N sodium chloride, potassium chloride, calcium chloride and/or magnesium acetate solutions corresponding to the desired concentration stages.

EP 0 613 688 B2 discloses a process enabling the individual adaptation of the composition of the dialysis liquid to different therapeutic requirements by using a basis concentrate mainly comprising sodium chloride and sodium hydrogencarbonate.

For the reasons stated above, the creation of a plasma-adapted, isotonic and balanced electrolyte solution that avoids the drawbacks of existing balanced electrolyte solutions as far as possible was desirable. Therefore, it was the object of the present invention to provide an isotonic, plasma-adapted balanced electrolyte solution that does not lead to infusion-induced disturbances of the homeostasis of the electrolyte and acid-base balance and shows a high local tolerability. Surprisingly, it has been found that this object is achieved by a balanced aqueous electrolyte solution as defined in claim 1. In addition, it has surprisingly been found that the electrolyte solution according to the invention solves the above mentioned problems of the prior art and, in particular, does not induce local irritations of the blood vessels or of the tissue surrounding the infusion site.

Accordingly, in a first aspect, the present invention relates to a balanced aqueous electrolyte solution comprising the following proportions of ions: a) from 138 to 146 mmol/l sodium, b) from 4 to 5 mmol/l potassium, c) from 0.5 to 2.0 mmol/l calcium, d) from 1.0 to 1.5 mmol/l magnesium, e) from 100 to 108 mmol/l chloride, f) from 0.5 to 1.5 mmol/l phosphate, g) from 18 to 26 mmol/l gluconate, and h) from 20 to 28 mmol/l acetate.

Preferred embodiments of the balanced electrolyte solution according to the invention comprise proportions of ions that independently correspond to at least one of the following concentrations: a) from 140 to 144 mmol/l sodium, and/or b) from 4.3 to 4.7 mmol/l potassium, and/or c) from 1.0 to 1.5 mmol/l calcium, and/or d) from 1.1 to 1.4 mmol/l magnesium, and/or e) from 102 to 106 mmol/l chloride, and/or f) from 0.8 to 1.2 mmol/l phosphate, and/or g) from 20 to 24 mmol/l gluconate, and/or h) from 22 to 26 mmol/l acetate.

It is further preferred that the balanced aqueous electrolyte solution has a pH within a range of from 5.0 to 8.0, more preferably from 6.0 to 7.0. More preferably, the balanced electrolyte solution according to the invention has an osmolality of from 280 to 300 mosmol/kg of $H_2O$.

It has been found advantageous to compose electrolyte mixtures in a solid form that can provide electrolyte solutions according to the invention by dissolving them in water. This simplifies the shipping, since the weight and volume of the solvent need not be shipped along. Further, an increase of stability and shelf life is achieved in this way.

The present invention further relates to an electrolyte mixture comprising the following proportions of ions: a) from 24.5 to 25.9% by weight sodium, b) from 1.21 to 1.51% by weight potassium, c) from 0.15 to 0.61% by weight calcium, d) from 0.19 to 0.28% by weight magnesium, e) from 27.3 to 29.5% by weight chloride, f) from 0.18 to 0.54% by weight phosphate, g) from 27.1 to 39.1% by weight gluconate, and h) from 9.10 to 12.7% by weight acetate, the percentages by weight each being based on the total weight of the electrolyte mixture.

According to the invention, it is advantageous to employ salts that are recommended and covered by monographs in relevant pharmacopeias, such as the European Pharmacopeia and the United States Pharmacopeia, among others.

Therefore, in a preferred embodiment, salts are employed that are selected from the group comprising sodium chloride, sodium acetate×3$H_2O$, sodium hydrogen-phosphate×2$H_2O$, D-gluconic acid sodium salt, potassium chloride, potassium acetate, calcium D-gluconate×$H_2O$, and magnesium chloride×6$H_2O$.

The electrolyte mixture according to the invention can be converted to the electrolyte solution according to the invention by dissolving in water and adjusting the pH value.

Therefore, the invention further relates to a process for preparing the balanced aqueous electrolyte solution according to the invention, comprising the steps of: (i) dissolving the electrolyte mixture according to the invention in an amount of water sufficient to adjust the molar concentrations of the respective electrolytes; and (ii) adjusting the solution to a pH value within a range of from 5.0 to 8.0.

Due to its plasma-adapted and balanced composition, isotonicity and non-problematic local tolerability, the electrolyte solution according to the invention is very well suitable as an infusion solution, not only for intravenous, but also for subcutaneous administration ("hypodermoclysis"). Therefore, the present invention relates to the use of the balanced aqueous electrolyte solution as an intravenous or subcutaneous infusion solution. As such, it has been found that it can be advantageously employed for treating hypotonic or isotonic dehydration, for treating extracellular fluid losses, hypovolemia or shock, and for rehydrating the interstitial space after colloidal volume replacement, or as a carrier solution for compatible electrolytes, nutrients and medicaments.

Therefore, the invention further relates to a medicament comprising the balanced aqueous electrolyte solution and optionally one or more further components selected from the group consisting of amino acids, carbohydrates, vitamins, minerals, hydroxyethyl starch, gelatin, albumin and drugs intended for infusion, preferably selected from the group consisting of antibiotics, analgetics, sedatives, neuroleptics, antiemetics, opiates, muscle relaxants, catecholamines, and other drugs with cardiovascular action.

The medicament according to the invention is preferably a medicament for treating hypotonic or isotonic dehydration, for treating extracellular fluid losses, for treatment in hypovolemia or shock, and for rehydrating the interstitial space after colloidal volume replacement.

The present invention further relates to the use of the balanced aqueous electrolyte solution as a topical rinsing solution, for example, for irrigation and cleaning during surgical operations, for the irrigation and cleaning of wounds and burns, for the irrigation of body cavities, for eye rinsing, for the rinsing and cleaning of instruments, and in stoma care, or as a carrier solution for compatible electrolytes, nutrients and medicaments.

EXAMPLES

The Examples stated in the following Table 2 are electrolyte solutions according to the invention.

TABLE 2

| | Preparation Examples | | | |
|---|---|---|---|---|
| Components | Example 1: | Example 2: | Example 3: | Example 4: |
| Sodium chloride | 5.815 g | 6.195 g | 5.639 g | 5.902 g |
| Sodium acetate × 3$H_2O$ | 3.266 g | 2.314 g | 2.382 g | 3.539 g |
| Sodium dihydrogenphosphate × 2$H_2O$ | 0.156 g | 0.156 g | 0.156 g | 0.234 g |
| D-Gluconic acid sodium salt | 3.817 g | 4.799 g | 5.454 g | 3.381 g |
| Potassium chloride | 0.298 g | — | 0.186 g | 0.186 g |
| Potassium acetate | — | 0.491 g | 0.245 g | 0.196 g |
| Calcium D-gluconate × $H_2O$ | 0.561 g | 0.897 g | 0.224 g | 0.561 g |
| Magnesium chloride × 6$H_2O$ | 0.203 g | 0.203 g | 0.305 g | 0.254 g |
| Water for injection | ad 1000 ml | ad 1000 ml | ad 1000 ml | ad 1000 ml |

The above stated substances are completely dissolved in water for injection in the amounts as stated for the Examples with stirring. Thereafter, the pH value is adjusted to pH=6.5 with a mixture of 10 ml of 2 N hydrochloric acid and 5 ml of 2 N acetic acid, the volume is filled up to 1000 ml with water for injection, and the solution is bottled into infusion glass jars at 250 ml, provided with a stopper and flanged. The jars are sterilized in a known manner according to the prior art (e.g., 20 minutes at 121° C.).

The invention claimed is:

1. A balanced aqueous electrolyte solution, comprising the following proportions of ions:
   a) from 138 to 146 mmol/l sodium,
   b) from 4 to 5 mmol/l potassium,
   c) from 0.5 to 2.0 mmol/l calcium,
   d) from 1.0 to 1.5 mmol/l magnesium,
   e) from 100 to 108 mmol/l chloride,
   f) from 0.5 to 1.5 mmol/l phosphate,
   g) from 18 to 26 mmol/l gluconate, and
   h) from 20 to 28 mmol/l acetate.

2. The balanced aqueous electrolyte solution according to claim 1, comprising from 140 to 144 mmol/l sodium.

3. The balanced aqueous electrolyte solution according to claim 1, comprising from 4.3 to 4.7 mmol/l potassium.

4. The balanced aqueous electrolyte solution according to claim 1, comprising from 1.0 to 1.5 mmol/l calcium.

5. The balanced aqueous electrolyte solution according to claim 1, comprising from 1.1 to 1.4 mmol/l magnesium.

6. The balanced aqueous electrolyte solution according to claim 1, comprising from 102 to 106 mmol/l chloride.

7. The balanced aqueous electrolyte solution according to claim 1, comprising from 0.8 to 1.2 mmol/l phosphate.

8. The balanced aqueous electrolyte solution according to claim 1, comprising g) from 20 to 24 mmol/l gluconate.

9. The balanced aqueous electrolyte solution according to claim 1, comprising h) from 22 to 26 mmol/l acetate.

10. The balanced aqueous electrolyte solution according to claim 1, characterized by having a pH within a range of from 5.0 to 8.0.

11. The balanced aqueous electrolyte solution according to claim 1, characterized by having a pH within a range of from 6.0 to 7.0.

12. An electrolyte mixture, comprising the following proportions of ions:
   a) from 24.5 to 25.9% by weight sodium,
   b) from 1.21 to 1.51% by weight potassium,
   c) from 0.15 to 0.61% by weight calcium,
   d) from 0.19 to 0.28% by weight magnesium,
   e) from 27.3 to 29.5% by weight chloride,
   f) from 0.18 to 0.54% by weight phosphate,
   g) from 27.1 to 39.1% by weight gluconate, and
   h) from 9.10 to 12.7% by weight acetate, the percentages by weight each being based on the total weight of the electrolyte mixture.

13. A process for preparing the balanced aqueous electrolyte solution according to claim 1, comprising the steps of:
   dissolving the electrolyte mixture according to claim 12 in an amount of water sufficient to adjust the molar concentrations of the respective electrolytes; and
   adjusting the solution to a pH value within a range of from 5.0 to 8.0.

14. The balanced aqueous electrolyte solution according to claim 1, wherein the solution is as an intravenous or subcutaneous infusion solution.

15. A medicament comprising the balanced aqueous electrolyte solution according to claim 1 and optionally one or more further components selected from the group consisting of amino acids, carbohydrates, vitamins, minerals, hydroxyethyl starch, gelatin, albumin and drugs intended for infusion.

16. A method for treating hypotonic or isotonic dehydration, for treating extracellular fluid losses, for treatment in hypovolemia or shock, or for rehydrating the interstitial space after colloidal volume replacement comprising intravenously or subcutaneously administering the medicament of claim 15 into an individual.

17. The balanced aqueous electrolyte solution according to claim 1, wherein the solution is a topical rinsing solution for irrigation and cleaning during surgical operations, for the irrigation and cleaning of wounds and burns, for the irrigation of body cavities, for eye rinsing, for the rinsing and cleaning of instruments, or for stoma care.

18. The balanced electrolyte solution according to claim 1, wherein the solution is a carrier solution for compatible electrolytes, nutrients and medicaments.

* * * * *

UNITED STATES PATENT AND TRADEMARK OFFICE
CERTIFICATE OF CORRECTION

PATENT NO. : 8,445,029 B2
APPLICATION NO. : 13/201321
DATED : May 21, 2013
INVENTOR(S) : Michael Boll It is certified that error appears in the above-identified patent and that said Letters Patent is hereby corrected as shown below:

In the Claims:

Col. 8, line 17, "...claim 1, wherein the solution is as an intravaneous or subcu-..." should read --...claim 1, wherein the solution is an intraveneous subcu-...--

Signed and Sealed this
Twenty-third Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,445,029 B2
APPLICATION NO.    : 13/201321
DATED              : May 21, 2013
INVENTOR(S)        : Michael Boll Page 1 of 1

It is certified that error appears in the above-identified patent and that said Letters Patent is hereby corrected as shown below:

In the Claims:

Col. 8, line 17, "...claim 1, wherein the solution is as an intravaneous or subcu-..." should read --...claim 1, wherein the solution is an intravenous subcu-...--

This certificate supersedes the Certificate of Correction issued July 23, 2013.

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,445,029 B2 | Page 1 of 1 |
| APPLICATION NO. | : 13/201321 | |
| DATED | : May 21, 2013 | |
| INVENTOR(S) | : Michael Boll | |

It is certified that error appears in the above-identified patent and that said Letters Patent is hereby corrected as shown below:

In the Claims:

Col. 8, line 17, "...claim 1, wherein the solution is as an intravaneous or subcu-..." should read --...claim 1, wherein the solution is an intravenous or subcu-...--

This certificate supersedes the Certificate of Correction issued July 23, 2013 and October 15, 2013.

Signed and Sealed this
Twenty-fourth Day of December, 2013

Margaret A. Focarino
*Commissioner for Patents of the United States Patent and Trademark Office*